(12) United States Patent
Nam et al.

(10) Patent No.: US 10,519,480 B2
(45) Date of Patent: Dec. 31, 2019

(54) METHOD FOR SELECTIVELY PRODUCING GINSENOSIDE RD FROM SAPONINS OF GINSENG THROUGH ENZYMATIC METHOD

(71) Applicant: AMOREPACIFIC CORPORATION, Seoul (KR)

(72) Inventors: Gi Baeg Nam, Yongin-si (KR); Dong Hyun Kim, Yongin-si (KR); Yong Deog Hong, Yongin-si (KR); Jun Seong Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/769,995

(22) PCT Filed: Oct. 21, 2016

(86) PCT No.: PCT/KR2016/011905
§ 371 (c)(1),
(2) Date: Apr. 20, 2018

(87) PCT Pub. No.: WO2017/069565
PCT Pub. Date: Apr. 27, 2017

(65) Prior Publication Data
US 2018/0320212 A1 Nov. 8, 2018

(30) Foreign Application Priority Data

Oct. 22, 2015 (KR) .................. 10-2015-0147354

(51) Int. Cl.
*C12P 33/16* (2006.01)
*C07H 17/00* (2006.01)
*C07J 17/00* (2006.01)
*C12P 19/44* (2006.01)

(52) U.S. Cl.
CPC .............. *C12P 33/16* (2013.01); *C07H 17/00* (2013.01); *C07J 17/00* (2013.01); *C12P 19/44* (2013.01); *C12Y 302/01004* (2013.01)

(58) Field of Classification Search
None
See application file for complete search history.

(56) References Cited

FOREIGN PATENT DOCUMENTS

| CN | 1477205 A | 2/2004 |
|---|---|---|
| KR | 10-2009-0061107 A | 6/2009 |
| KR | 10-2011-0123311 A | 11/2011 |
| KR | 10-2013-0003944 A | 1/2013 |
| KR | 10-2014-0006331 A | 1/2014 |

OTHER PUBLICATIONS

Lee et al. Process Biochemistry (2012) 47: 538-543 (Year: 2012).*
Sunwoo et al. Biotechnol. Lett. (2013) 35: 1017-1022 (Year: 2013).*
Cho et al. J. Ginseng Res. (2010) 34(2): 113-121 (Year: 2010).*
Palaniyandi et al. Biotechnol. Bioprocess Engineering (2015) 20: 608-613 (Year: 2015).*
Lu et al. Innovative Food Sci. and Emerging Technolgies (2014) 22: 95-101 (Year: 2014).*
Sung-Ryong Ko et al., "Marked Production of Ginsenosides Rd, $F_2$, $Rg_3$, and Compound K by Enzymatic Method," Chem. Pharm. Bull., Oct. 2007, pp. 1522-1527, vol. 55, No. 10.
International Search Report of PCT/KR2016/011905 dated Feb. 15, 2017.

* cited by examiner

*Primary Examiner* — Susan M Hanley
(74) *Attorney, Agent, or Firm* — Sughrue Mion, PLLC

(57) ABSTRACT

The present invention relates to a method for selectively producing ginsenoside Rd, which is originally present in ginseng in a trace amount, from panaxadiol-type saponins of ginseng, and more specifically to a method capable of obtaining a desired target compound, that is, ginsenoside Rd, in high yields, by treating a panaxadiol-type saponin obtained from ginseng, with particular enzymes to structurally convert the saponins.

7 Claims, 1 Drawing Sheet

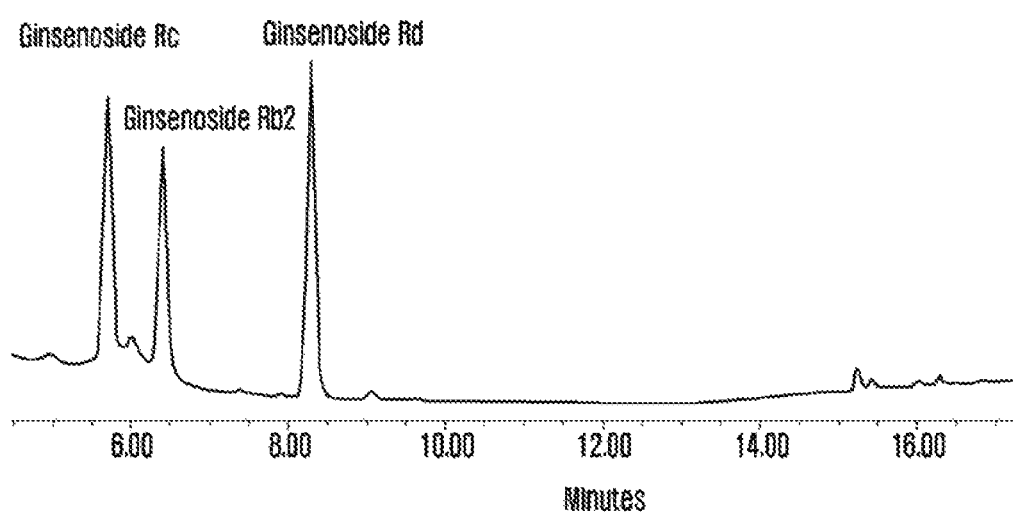

METHOD FOR SELECTIVELY PRODUCING GINSENOSIDE RD FROM SAPONINS OF GINSENG THROUGH ENZYMATIC METHOD

CROSS REFERENCE TO RELATED APPLICATIONS

This application is a National Stage of International Application No. PCT/KR2016/011905 filed Oct. 21, 2016, claiming priority based on Korean Patent Application No. 10-2015-0147354 filed Oct. 22, 2015.

TECHNICAL FIELD

The present invention relates to a method for selectively producing ginsenoside Rd, which is originally present in ginseng in a trace amount, from ginsenoside Rb1 which is saponins of ginseng, and more specifically to a method capable of obtaining a desired target compound, that is, ginsenoside Rd, in high yields, by treating a panaxadiol-type saponin, ginsenoside Rb1, obtained from ginseng, with particular enzymes to structurally convert the saponins.

BACKGROUND ART

Ginseng saponin has a unique chemical structure different from that of saponin found in other plants.

Thus, its pharmacological efficacy is unique, and thus it is also called "ginsenoside" in the sense of ginseng glycoside. Specific types of ginseng saponins include panaxadiol-type ginsenosides Rb1, Rb2, Rc, Rd, compound K, compound Mc, compound O, etc., and panaxatriol-type ginsenosides Re, Rf, Rg1, Rg3, Rg5, Rh1, Rh2, etc., and each of these ginseng saponins exhibit different efficacies.

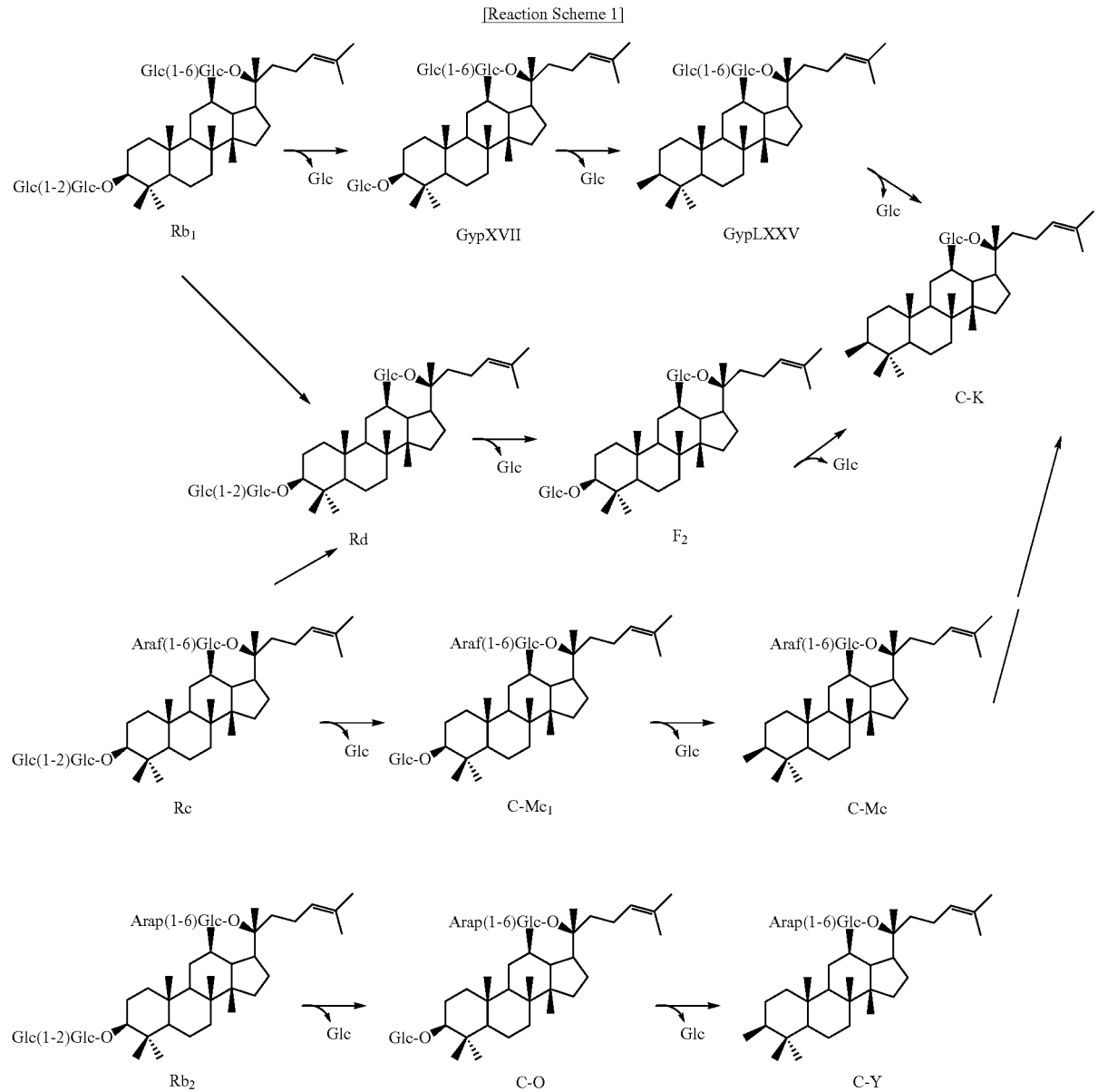

[Reaction Scheme 1]

As shown in the Reaction Scheme 1, particularly, since ginsenosides Rb1, Rb2, Rc, etc., which are panaxadiol type saponins, can be converted into other ginseng saponins by metabolism of microorganisms, a method using enzymes has been used for a long time as a method of converting ginseng saponin into other kinds of specific ginseng saponins.

However, for the conversion reaction using enzymes in the past, non-specificity of enzymes for a substrate is large and thus an extremely large amount of enzyme should be used relative to the saponin substrate used. Further, the enzymatic reaction is not completed with a desired ginseng saponin, but an additional reaction occurs nonspecifically. Thus, since other ginseng saponins were variously produced without being converted only to the desired ginseng saponin, the yield of the desired ginseng saponin was extremely low.

In addition, conventional methods of obtaining ginseng saponins do not convert only to a desired specific ginseng saponin, but provide a technical solution of obtaining various converted ginseng saponins by extraction or the like and then purifying the resultant to isolate only desired ginseng saponins.

However, since these conventional methods require additional cost and time associated with the purification in order to obtain a pure specific ginseng saponin. Therefore, the selling price of ginseng saponins is inevitably increased, and there is a limit to applying a large amount of ginseng saponins to related products.

Furthermore, if the enzyme reaction occurs nonspecifically, nonselective removal of sugar in ginsenoside Rd allows it to convert into ginsenoside F2 and compound K, and thus it becomes difficult to obtain intermediate metabolites such as ginsenoside Rd and the like in high yield.

PRIOR ART LITERATURE

Patent Literature

1. Korean Patent Laid-Open Publication No. 10-2014-0006331 (published on Jan. 16, 2014)

DETAILED DESCRIPTION OF THE INVENTION

Technical Problem

It was expensive to acquire a specific ginseng saponin by a conventional method and also it was difficult to obtain the desired ginseng saponin in large quantities. Therefore, there is a need to develop a production method that can produce a large amount of target ginseng saponins and can save costs.

Accordingly, an object of the present invention is to provide a conversion method of ginseng saponin which can obtain a desired specific ginseng saponin in a high yield and also can be easily carried out Technical Solution In order to achieve the above object, the present invention provides a method for producing ginsenoside Rd by converting saponins of ginseng using at least one enzyme selected from the group consisting of pectinase and cellulase isolated from genus *Trichoderma*.

Advantageous Effects

By using the method for converting to ginseng saponins according to the present invention, the desired ginseng saponin can be easily produced with high yield.

BRIEF DESCRIPTION OF DRAWINGS

FIG. 1 shows the results of confirming ginsenoside Rd produced after the conversion reaction of ginseng saponin though silica gel column chromatography.

DETAILED DESCRIPTION OF THE EMBODIMENTS

The present invention relates to a method for selectively producing ginsenoside Rd (chemical formula 1) from saponins of ginseng, particularly ginsenoside Rb1, which is a panaxadiol-type saponin, by an enzymatic method.

[Chemical Formula 1]

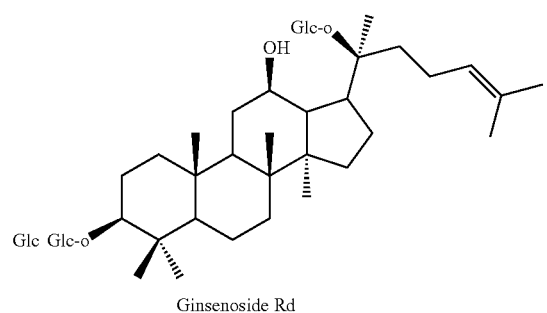

Ginsenoside Rd

According to the method of the present invention, the conversion from saponin of ginseng to a desired ginseng saponin can be efficiently carried out by using enzymes derived from microorganisms, thereby obtaining ginsenoside Rd in high yield.

Specifically, the enzyme used in the present invention is desirably obtained from at least one microorganism selected from the group consisting of the microorganisms belonging to the genus *Trichoderma*, particularly *Trichoderma aggressivum*, *Trichoderma harzianum*, *Trichoderma reesei* and *Trichoderma viride*, and those obtained from *Trichoderma reesei* are most preferred.

In addition, the enzyme used in the present invention may be lactase, cellulase, beta-galactosidase, pectinase, naringinase, hemicellulase, or a mixture thereof, isolated from a microorganism of the genus *Trichoderma*, and pectinase, cellulase, or a mixture thereof are preferred.

Even the same type of enzyme that performs mostly the same function, the site where the enzyme functions specifically in the substrate varies depending on the species of the microorganism from which the enzyme is derived, resulting in a difference in substrate specificity. Therefore, in the present invention, it is most desirable to use at least one selected from the group consisting of pectinase and cellulase obtained from *Trichoderma reesei*.

In the present invention, saponin of ginseng is dissolved in a solvent in an amount of 0.01 to 20% by weight, and then the saponin is converted into the desired ginseng saponin by an enzymatic method using the above-mentioned enzyme. The solvents used here are preferably those that do not inhibit the activity of the enzyme, for example, an aqueous solvent such as water or a buffer solution, or a mixture of an aqueous solvent and an organic solvent such as water or a buffer solution can be used. Specifically, the buffer solution used here may be acetic acid, citric acid, phosphoric acid, citric acid-phosphoric acid, or the like, and the organic solvent may be acetonitrile, dioxane, dimethyl sulfoxide, methanol, ethanol, 1-propanol, 2-propanol, or the like. The pH range of the solvent that can be used is preferably 2.5 to 7.5, more preferably 3.5 to 5.5.

In the method of the present invention, the enzyme to be used is added in an amount of preferably 1 to 500% by weight, more preferably 10 to 400% by weight, still more preferably 10 to 200% by weight, based on the amount of the substrate used.

The reaction temperature must be a temperature condition under which no enzyme inactivation occur, but the temperature is maintained in the range of preferably 30 to 60° C., more preferably 35 to 60° C., still more preferably 40 to 55° C.

Furthermore, the reaction time is not particularly limited as long as it is a period during which the activity of the enzyme is maintained, but it is desirable to perform the reaction while stirring for 1 to 120 hours, preferably 1 to 72 hours, more preferably 1 to 48 hours, still more preferably 1 to 24 hours.

Subsequently, a reaction solution containing a large amount of ginsenoside Rd can be obtained by inactivating the enzyme using a known method such as heating in a boiling water bath.

DETAILED DESCRIPTION OF THE EMBODIMENTS

Hereinafter, the present invention will be described in detail by way of Examples. However, these Examples are given for illustrative purposes only, and are not intended to limit the scope of the invention thereto.

[Reference Example 1] Production of Ginseng Purified Saponin 20 l of ethanol was added to 2 kg of red ginseng, white ginseng, fresh ginseng, tiny-sized ginseng or leaves, flowers and fruits of ginseng, and extracted three times under reflux and then immersed at 15° C. for 6 days. Thereafter, the residue and the filtrate were isolated through filter cloth-filtration and centrifugation, and the isolated filtrate was concentrated under reduced pressure. The extract obtained was suspended in water, and then extracted five times with 1 l of ether to remove a pigment. The aqueous layer was extracted three times with 1 l of 1-butanol. The total 1-butanol layer thus obtained was treated with 5% KOH, washed with distilled water and then concentrated under reduced pressure to obtain 1-butanol extract, which was dissolved in a small amount of methanol, and then added to a large amount of ethyl acetate. The resulting precipitate was dried to thereby obtain 40 to 80 g of ginseng purified saponin (including ginsenoside Rb1, Rb2, Rc, Rd, Re, Rg1, Rf, etc.).

[Example 1] Production of Ginsenoside Rd Through Enzymatic Reaction 10 g of ginseng purified saponin (including ginsenoside Rb1, Rb2, Rc, Rd, Re, Rg1, Rf, etc.) of the Reference Example 1 was dissolved in 1 @ of water.

Thereafter, pectinase isolated from *Trichoderma reesei* was added to the above mixed solution in an amount of 200% by weight relative to the substrate, and the mixture was reacted at 30° C. for 48 hours. When the substrate was completely disappeared by periodic confirmation by thin layer chromatography, the enzyme was inactivated by heating in a boiling water bath for 10 minutes, thereby completing the reaction. Finally, ethyl acetate or ethanol was added to the reaction solution at a ratio of 1:1 (ratio of volume to the reaction solution), extracted three times, concentrated and then subjected to silica gel column chromatography (chloroform:methanol=9:1) to isolate ginsenoside Rd (FIG. 1).

2.66 g of ginsenoside Rb1, 0.73 g of ginsenoside Rb2, 1.23 g of ginsenoside Rc and 0.38 g of ginsenoside Rd were present in 10 g of the *ginseng* saponin of Reference example 1 used. In the mixed solution obtained after the enzymatic reaction, ginsenoside Rb1 was present in an amount of 0.009 g, whereas ginsenoside Rd was present in an amount of 2.57 g, and ginsenosides Rb 2 and Rc were present in an amount of 0.73 g and 1.23 g, respectively. This means that ginsenoside Rd is selectively converted from ginsenoside Rb1. In particular, it indicates that 2.19 g of ginsenoside Rd is produced from ginsenoside Rb1 and the conversion rate to ginsenoside Rd is 95% or more. On the other hand, ginsenosides Rb2 and Rc were present in the same amount even after the enzymatic reaction, indicating that they remain in a state where conversion is not performed.

The invention claimed is:
1. A method for producing ginsenoside Rd of the following chemical formula 1 from ginsenoside Rb1,
    said method comprising contacting a substrate comprising ginsenoside Rb1 with pectinase obtained from *Trichoderma reesei* thereby converting the ginsenoside Rb1 to ginsenoside Rd:

Chemical Formula 1

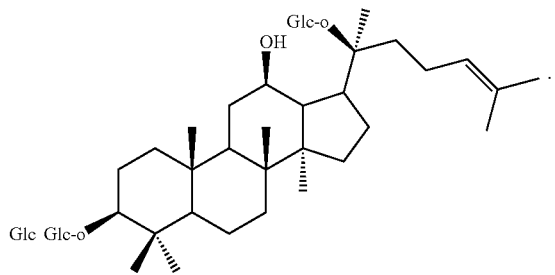

2. The method according to claim 1, wherein the substrate comprising ginsenoside Rb1 is a *ginseng* saponin.
3. The method according to claim 2, wherein the method comprises the steps of:
    1) contacting the *ginseng* saponin in an aqueous solvent or a mixed solution of an aqueous solvent and an organic solvent with the pectinase, and allowing the converting undergoes thereby producing a reaction mixture comprising ginsenoside Rd as a conversion product;
    2) inactivating the pectinase in the reaction mixture of 1) thereby completing the conversion reaction; and
    3) adding ethyl acetate or ethanol to the reaction mixture obtained in 2), followed by extraction and concentration, thereby isolating ginsenoside Rd.
4. The method according to claim 1, wherein the pectinase is added in an amount of 10 to 400% by weight based on the amount of the substrate.

5. The method according to claim 1, wherein the converting of 1) is carried out at a temperature of 35 to 60° C.

6. The method according to claim 3, wherein the converting of 1) is carried out for 1 to 48 hours.

7. The method according to claim 3, wherein the aqueous solvent or the mixed solution of an aqueous solvent and an organic solvent has a pH in the range of 3.5 to 5.5.

* * * * *